(12) United States Patent
Schermeier et al.

(10) Patent No.: US 8,353,288 B2
(45) Date of Patent: Jan. 15, 2013

(54) PATIENT CARE UNIT WITH A RECLINING SURFACE

(75) Inventors: Olaf Schermeier, Lübeck (DE); Hans-Ulrich Hansmann, Barnitz (DE); Henning Gerder, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1264 days.

(21) Appl. No.: 12/129,098

(22) Filed: May 29, 2008

(65) Prior Publication Data

US 2008/0295836 A1 Dec. 4, 2008

(30) Foreign Application Priority Data

May 31, 2007 (DE) .......................... 10 2007 025 487

(51) Int. Cl.
- A61M 15/00 (2006.01)
- A61M 16/00 (2006.01)
- A62B 7/00 (2006.01)
- A62B 9/00 (2006.01)

(52) U.S. Cl. ......... 128/200.24; 128/204.18; 128/204.21; 128/202.22; 128/845; 600/300; 600/301

(58) Field of Classification Search ............. 128/200.24, 128/202.22, 845, 204.18, 204.21; 600/300, 600/301
See application file for complete search history.

(56) References Cited

U.S. PATENT DOCUMENTS

| | | | | |
|---|---|---|---|---|
| 4,217,993 A * | 8/1980 | Jess et al. | .......................... | 222/14 |
| 5,335,651 A * | 8/1994 | Foster et al. | ............. | 128/202.13 |
| 5,337,845 A * | 8/1994 | Foster et al. | ..................... | 180/11 |
| 5,370,111 A * | 12/1994 | Reeder et al. | ............. | 128/202.13 |
| 5,375,604 A * | 12/1994 | Kelly et al. | ................... | 600/484 |
| 5,431,171 A * | 7/1995 | Harrison et al. | ............. | 600/511 |
| 5,687,717 A * | 11/1997 | Halpern et al. | ............... | 600/300 |
| 6,158,430 A * | 12/2000 | Pfeiffer et al. | ............. | 128/202.27 |
| 6,221,012 B1 * | 4/2001 | Maschke et al. | ............. | 600/301 |
| 6,360,389 B1 * | 3/2002 | Gallant et al. | .................... | 5/658 |
| 6,749,566 B2 | 6/2004 | Russ | | |
| 6,993,799 B2 * | 2/2006 | Foster et al. | ...................... | 5/510 |
| 7,636,966 B2 * | 12/2009 | Gallant et al. | .................... | 5/600 |
| 7,647,926 B2 * | 1/2010 | Gerder et al. | ............. | 128/204.22 |
| 7,708,690 B2 * | 5/2010 | Beckmann et al. | ........... | 600/300 |
| 7,771,386 B2 * | 8/2010 | Eggers et al. | ................... | 604/67 |
| 2003/0140929 A1 * | 7/2003 | Wilkes et al. | ................ | 128/898 |
| 2003/0144878 A1 * | 7/2003 | Wilkes et al. | ...................... | 705/2 |
| 2004/0182392 A1 * | 9/2004 | Gerder et al. | ............. | 128/204.22 |
| 2005/0267339 A1 | 12/2005 | Beckmann et al. | | |
| 2006/0107463 A1 * | 5/2006 | Foster et al. | ...................... | 5/620 |
| 2007/0113342 A1 * | 5/2007 | Foster et al. | ...................... | 5/600 |
| 2007/0201992 A1 * | 8/2007 | Mernoe | .......................... | 417/321 |

\* cited by examiner

*Primary Examiner* — Lynne Anderson
*Assistant Examiner* — Bradley Philips
(74) *Attorney, Agent, or Firm* — McGlew and Tuttle, P.C.

(57) ABSTRACT

A patient care unit (1) with a reclining surface has one or more docking devices designed as inductive coupling sites (7) for medical technical devices (10, 11, 12), which consume electrical energy and can be connected to the patient care unit. The inductive coupling sites (7) also supply the patient care unit (1) with electrical energy by means of an external line connection, which is likewise coupled inductively with the patient care unit (1).

19 Claims, 2 Drawing Sheets

PATIENT CARE UNIT WITH A RECLINING SURFACE

CROSS REFERENCE TO RELATED APPLICATIONS

This application claims the benefit of priority under 35 U.S.C. §119 of German Patent Application DE 10 2007 025 487.5 filed May 31, 2007, the entire contents of which are incorporated herein by reference.

FIELD OF THE INVENTION

The present invention pertains to a patient system with a patient care unit with a reclining surface and with one or more docking devices designed as inductive coupling sites for medical technical devices which consume electric energy and can be connected to the patient care unit.

BACKGROUND OF THE INVENTION

A patient care unit with a reclining surface for accommodating a patient is known from DE 10 2004 025 797 B3. This prior-art patient care unit is equipped with means for receiving sensor signals of the patient and with means for sending the sensor signals to a cable connection for connecting the patient care unit to the supply network voltage, so that the sensor signals reach corresponding measuring or treating devices via the electrical supply network for analysis of the sensor signals.

An information network for the clinical area has become known from U.S. Pat. No. 6,749,566 B2, in which the physiological parameters measured at the patient are transmitted in a radio-based manner from individual devices at the patient into the network for further processing.

A flexible breathing gas or breathing tube for the mechanical respiration of a patient with a signal line extending along the flexible breathing gas tube and with a sensor means at the end of the flexible breathing tube, which end faces away from the respirator and faces the patient, is described in DE 103 12 881 B3. A contactless, especially inductive interface is arranged between the sensor means and the signal line.

The use of various medical technical devices in the vicinity of or directly at the patient is necessary during a medical treatment, for example, during surgery or during stay in an intensive care unit, in order to monitor or measure physiological or vital parameters of the patient and to supply the patient with life-preserving means, while the patient is, in general, on a patient care unit with a reclining surface, for example, on an operating table, during the treatment. The patient care unit may be equipped with additional functional elements, for example, with elements for the reclining surface, which elements can be adjusted by means of an electric motor.

Medical technical devices are, for example, patient monitors for detecting, processing and displaying physiological measured data. Medical technical devices are, for example, also electrically operated inhalers, respiration humidifiers or infusion pumps for dispensing and administering drugs.

It is common to such electrically operated medical technical devices that they are either supplied with electrical energy via a permanent line connection or they must be connected via a corresponding cable connection for recharging the internal energy storage unit with a separate, external power supply unit via a corresponding cable connection, as in the case of portable, non-stationary patient monitors.

SUMMARY OF THE INVENTION

The object of the present invention is to provide a patient care unit with a reclining surface, which makes it possible to connect medical technical devices directly to the patient care unit for electrical energy supply without a separate cable connection.

According to the invention, a patient system is provided comprising a patient care unit with a reclining surface and a docking device connected to the reclining surface. The docking device includes an inductive coupling site for inductive coupling. A medical technical device, which consumes electric energy, is provided including an inductive supply tap for inductively coupling the medical technical device to the patient care unit via the inductive coupling site. An external line connection is provided for supplying the patient care unit with electrical energy.

The present patient care unit is advantageously equipped with one or more docking devices designed as inductive coupling sites for medical technical devices which consume electrical energy and can be connected to the patient care unit, as well as with a line connection, which can likewise be connected inductively to the patient care unit, for the external electrical energy supply of the patient care unit.

The system may further comprise a flexible breathing tube wherein the external line connection for the electrical energy supply for the patient care unit comprises wire lines extending in a longitudinal direction of the flexible breathing tube.

The system may include a respirator wherein the flexible breathing tube is in a breathing line connection with a respirator.

The docking device may include an inductive feeding coupling site and the flexible breathing tube may be equipped with a tube inductive supply tap for inductively coupling to the inductive feeding coupling site for feeding energy into the inductive coupling site at the patient care unit.

The patient care unit may further comprise a supply bus provided in the patient care unit and connected to each of the inductive coupling site and the inductive feeding coupling site for supplying the inductive coupling site with electrical energy via the feeding coupling site.

The medical technical device may comprise one or more of a patient monitor, an infusion pump, and a portable monitor. The portable monitor and/or the infusion pump may be remotely controllable by means of the respirator or by means of a stationary monitor.

The patient system may also include an information network with a hospital information system and with an application server. The patient care unit may be connected to the application server via the information network.

The patient system may further comprise a portable monitor with a radio interface for a first data path into the information network via a wireless access node of the information network as well as with a second line-bound data path via a connection line with the feeding coupling site, the flexible breathing tube, a respirator and a line from the respirator into the information network.

The transmission path for the energy supply may also form a data transmission path.

Exemplary embodiments of the patient care unit will be explained below by means of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
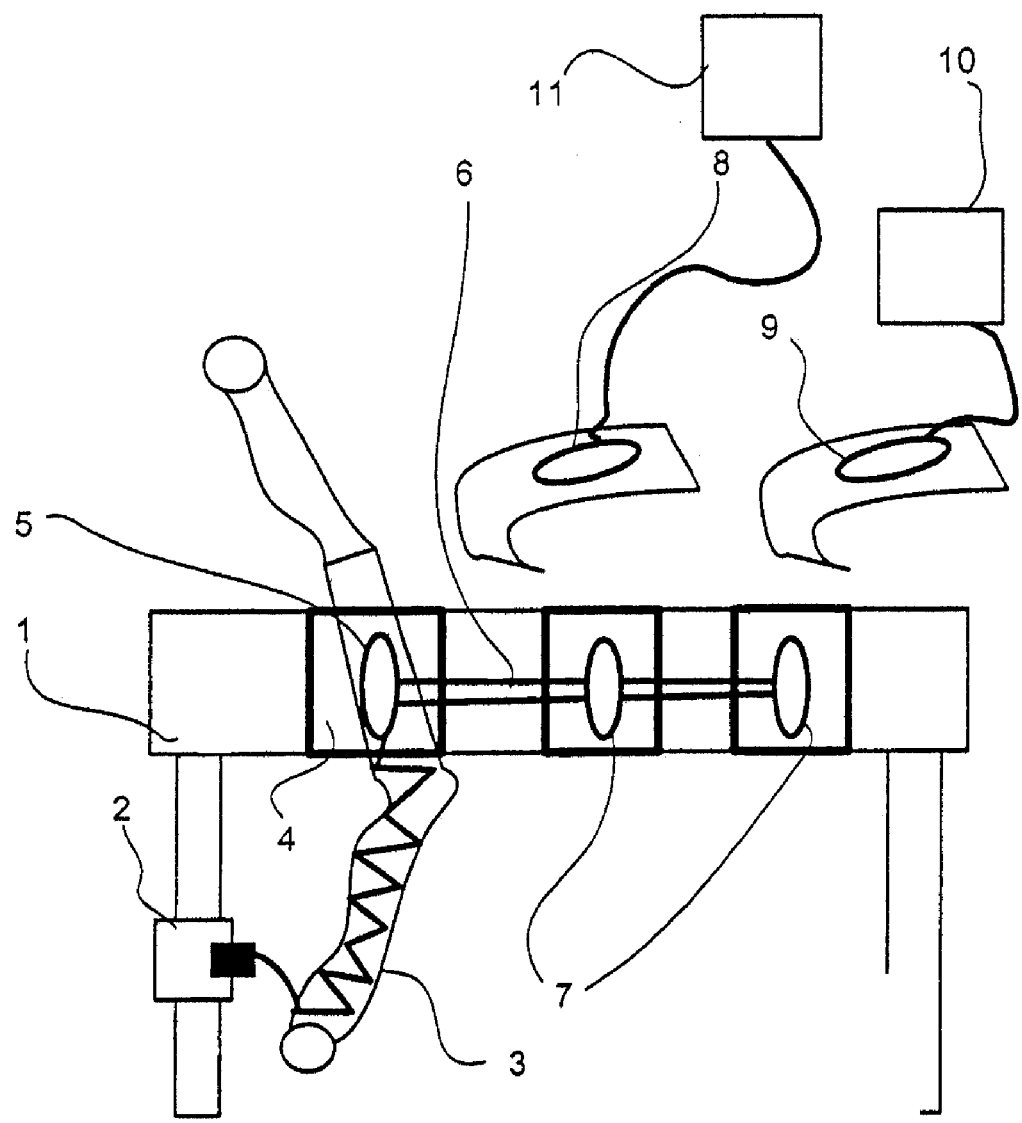
FIG. 1 is a schematic view of a patient care unit with a flexible breathing gas conduit or breathing tube.

Referring to the drawings in particular, FIG. 1 schematically shows the patient care unit 1 with a reclining surface for accommodating a patient. The respirator 2 is docked with the patient care unit 1 and supplies the patient with breathing gas via a flexible breathing tube 3. A two-wire line acting as a line connection for the electrical energy supply and optionally also for the data supply of the patient care unit 1 or of the devices connected to the patient care unit 1 is located in the flexible breathing tube 3. The external energy supply for the flexible breathing tube 3 takes place via a plug connection from the respirator 2.

The flexible breathing tube 3 is equipped with an inductive feed point 5 for feeding energy into the feed coupling site 4 at the patient care unit 1. A supply bus 6 for electrical energy supply for the coupling sites 7 for the inductive energy supply via supply taps 8, 9 of two medical technical devices 10, 11, for example, a patient monitor and an infusion pump, is located in the patient care unit 1.

Figure 2:
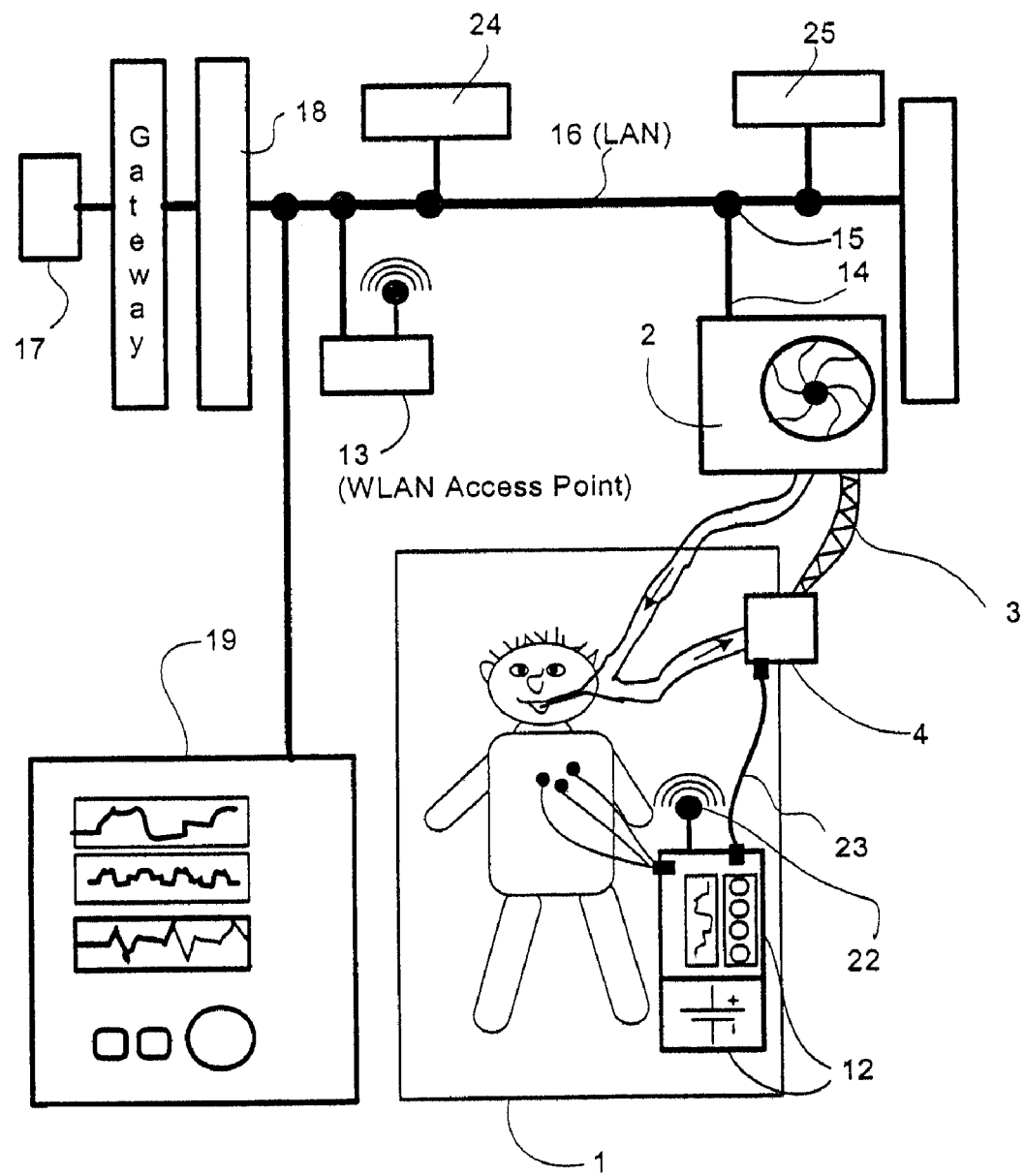
FIG. 2 is a schematic view of a patient care unit in an expanded configuration with an information network in a hospital.

FIG. 2 shows the integration of a patient care unit 1 in an expanded configuration in an information network 16 in a hospital. The patient on the patient care unit 1 is equipped with a portable monitor 12 for detecting various physiological measured values from sensors, electrodes, etc., at the patient. The portable monitor 12 has an electrically rechargeable storage unit as well as a radio interface 22 for a first data path into the information network 16 via the wireless data access node 13 (WLAN Access Point).

The feed and coupling site 4 is used for the inductive energy and signal or data coupling.

The energy and data connection between the respirator 2 and the feeding coupling site 4 takes place via the flexible breathing tube 3. The signal transmission via a second, line-bound data path takes place via the connection line 23 and via the feed coupling site 4, the respirator 2 and line 14 from the respirator 2 and via the data node 15 into the information network 16.

The hospital information system 17 with patient data is connected to the information network 16 via a data path with an application server 18.

The stationary monitor 19 is likewise connected to the information network 16, so that both the patient data from the hospital information system 17 and the associated data of a certain portable monitor 12 for the corresponding patient can be merged in the stationary monitor 19.

The assignment of the data sent by radio from the portable monitor 12 (data path 1) takes place by comparison and validation with the data transmitted via the flexible breathing tube 3 (data path 2).

This makes possible the conflict-free parallel operation of a plurality of radio transmitters in one room, especially with a plurality of patients and a plurality of portable monitors 12.

The control data path, i.e., the second, line-bound data path, can be used during the initialization to avoid confusion, but also in case of failure of the radio connection as a signaling path to transmit trouble and status reports.

Monitoring data can be displayed on the display unit of the respirator 2 or data of the respirator 2 can be visualized on the display unit of the portable monitor 12 by means of the present arrangement.

It is also possible to display data of the respirator 2 and of the portable monitor 12 on the display unit of the stationary monitor 19. Two additional participants 24, 25 are shown by way of example in the information network 16.

While specific embodiments of the invention have been shown and described in detail to illustrate the application of the principles of the invention, it will be understood that the invention may be embodied otherwise without departing from such principles.

What is claimed is:

1. A patient system comprising:
   a patient care unit with a reclining surface and a docking device connected to said reclining surface, said docking device including an inductive coupling site for inductive coupling;
   a medical technical device which consumes electric energy, said medical device including an inductive supply tap for inductively coupling said medical technical device to the patient care unit via said inductive coupling site;
   an external line connection for supplying said patient care unit with electrical energy; and
   a flexible breathing tube wherein said external line connection for the electrical energy supply for said patient care unit comprises wire lines extending in a longitudinal direction of said flexible breathing tube.

2. A patient system in accordance with claim 1, further comprising a respirator wherein said flexible breathing tube is in a breathing line connection with said respirator.

3. A patient system in accordance with claim 1, wherein said docking device includes an inductive feeding coupling site and said flexible breathing tube is equipped with a tube inductive supply tap for inductively coupling to said inductive feeding coupling site as an inductive feeding site for feeding energy into said inductive coupling site at said patient care unit.

4. A patient system in accordance with claim 3, wherein said patient care unit further comprises a supply bus provided in said patient care unit and connected to each of said inductive coupling site and said inductive feeding coupling site for supplying said inductive coupling site with electrical energy via said feeding coupling site.

5. A patient system in accordance with claim 1, wherein said medical technical device comprises one of a patient monitor, an infusion pump, and a portable monitor.

6. A patient system in accordance with claim 4, further comprising an information network with a hospital information system and with an application server, said patient care unit being connected to said application server via said information network.

7. A patient system in accordance with claim 6, further comprising a portable monitor provided with a radio interface for a first data path into said information network via a wireless access node of said information network as well as with a second line-bound data path via a connection line with said feeding coupling site, said flexible breathing tube, a respirator and a line from said respirator into said information network.

8. A patient system in accordance claim 7, wherein a transmission path for the energy supply also forms a data transmission path.

9. A patient system in accordance with claim 8, wherein said portable monitor and/or a infusion pump are remotely controllable by means of said respirator or by means of a stationary monitor.

10. A patient system comprising:
    a patient care unit with a reclining surface, a supply bus fixed to said patient care unit and a docking device connected to said reclining surface, said docking device including an inductive coupling site for inductive coupling and an inductive feeding coupling site for inductive coupling and feeding power to said supply bus, said inductive coupling site being connected to said inductive feeding coupling site via said supply bus and said feeding coupling site feeding power to said inductive coupling site via said supply bus;
    a medical technical device which consumes electric energy, said medical device including an inductive supply tap for inductively coupling said medical technical device to said supply bus of said patient care unit via said inductive coupling site to receive electric energy therefrom; and
    an external line connection including an inductive supply tap for supplying said supply bus of said patient care unit with electrical energy via said inductive feeding coupling.

11. A patient care unit in accordance with claim 10, further comprising a flexible breathing tube wherein said external line connection for the electrical energy supply for said patient care unit comprises wire lines extending in a longitudinal direction of said flexible breathing tube.

12. A patient system in accordance with claim 11, further comprising a respirator wherein said flexible breathing tube is in a breathing line connection with a respirator and said external line provides an electrical supply connection via said respirator.

13. A patient system in accordance with claim 12, wherein said medical technical device comprises one of a patient monitor, an infusion pump, and a portable monitor.

14. A patient system in accordance with claim 13, further comprising an information network with a hospital information system and with an application server connected; and
    a portable monitor provided with a radio interface for a first data path into said information network via a wireless access node of said information network, said patient care unit being connected to said information network via said feeding coupling site, said external line connection of said flexible breathing tube, said respirator and a line from said respirator into said information network.

15. A patient system in accordance claim 14, wherein said external line connection provides a transmission path for energy supply and a data transmission path.

16. A patient system in accordance with claim 15, wherein said portable monitor and/or said infusion pump are remotely controllable by means of said respirator or by means of a stationary monitor.

17. A patient system comprising:
    a patient care unit with a reclining surface, a supply bus and a docking device connected to said reclining surface, said docking device including an inductive coupling site for inductive coupling connected to an inductive feeding coupling site for inductive coupling via a supply bus;
    a medical technical device which consumes electric energy, said medical device including an inductive supply tap for inductively coupling said medical technical device to the patient care unit via said inductive coupling site to receive electric energy therefrom;
    a flexible breathing tube with an external line connection providing a transmission path for supplying said patient care unit with electrical energy via said inductive feeding coupling and providing a data transmission path via said inductive feeding coupling wherein said external line connection for the electrical energy supply for said patient care unit comprises wire lines extending in a longitudinal direction of said flexible breathing tube; and
    a respirator wherein said flexible breathing tube is in a breathing line connection with the respirator and said external line provides an electrical supply connection via said respirator.

18. A patient system in accordance with claim 17, further comprising:
    an information network with a hospital information system and with an application server, said patient care unit being connected to said information network via said feeding coupling site, said external line connection of said flexible breathing tube, said respirator and a line from said respirator into said information network.

19. A patient system in accordance with claim 18, further comprising:
    a portable monitor provided with a radio interface for a first data path into said information network via a wireless access node of said information network and with a second portable monitor data path connected to said information network via said inductive coupling site, said bus, said inductive feeding coupling site, said external line connection of said flexible breathing tube, said respirator and a line from said respirator into said information network.

* * * * *